United States Patent
Corcoran et al.

(10) Patent No.: US 7,578,671 B2
(45) Date of Patent: Aug. 25, 2009

(54) ORTHODONTIC DEVICE FOR TREATING MALOCCLUSIONS

(75) Inventors: Kevin Corcoran, Corona, CA (US);
Terry Dischinger, Lake Oswego, OR (US); Hamid Sheikh, Chino, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 11/459,530

(22) Filed: Jul. 24, 2006

(65) Prior Publication Data
US 2007/0020577 A1    Jan. 25, 2007

Related U.S. Application Data

(60) Provisional application No. 60/702,142, filed on Jul. 25, 2005.

(51) Int. Cl.
*A61C 3/00* (2006.01)
*A61C 13/12* (2006.01)

(52) U.S. Cl. .......................... 433/19; 433/179

(58) Field of Classification Search ............. 433/18–19, 433/24, 7, 179
See application file for complete search history.

(56) References Cited

U.S. PATENT DOCUMENTS

| | | | |
|---|---|---|---|
| 2,262,108 A | 11/1941 | Linde | |
| 3,798,773 A | 3/1974 | Northcutt | |
| 4,382,783 A | 5/1983 | Rosenberg | |
| 4,462,800 A | 7/1984 | Jones | |
| 4,472,139 A | 9/1984 | Rosenberg | |
| 4,551,095 A * | 11/1985 | Mason | 433/19 |
| 4,618,324 A * | 10/1986 | Nord | 433/19 |
| 4,795,342 A | 1/1989 | Jones | |
| 5,066,226 A | 11/1991 | Summer | |
| 5,120,218 A | 6/1992 | Hanson | |
| 5,183,388 A | 2/1993 | Kumar | |
| 5,352,116 A | 10/1994 | West | |
| 5,378,147 A | 1/1995 | Mihailowitsch | |
| 5,562,445 A | 10/1996 | DeVincenzo et al. | |
| 5,620,321 A | 4/1997 | Thornburg et al. | |
| 5,632,618 A | 5/1997 | Jensen | |
| 5,645,423 A | 7/1997 | Collins, Jr. | |

(Continued)

FOREIGN PATENT DOCUMENTS

DE    203 15 857    12/2003

(Continued)

OTHER PUBLICATIONS

Claudio Salvatore (Authorized Officer); International Search Report and Written Opinion; Dec. 18, 2006; 12 pages; European Patent Office.

(Continued)

*Primary Examiner*—John J Wilson
*Assistant Examiner*—Heidi M Eide
(74) *Attorney, Agent, or Firm*—Wood, Heron & Evans, L.L.P.

(57) ABSTRACT

An orthodontic device treats malocclusions using a telescopic rod fixed to a molar on the upper arch and a molar on a lower arch. The telescopic rod lengthens and shortens during opening and closing of the jaw. The telescopic rod encourages the patient to properly position their jaw causing adaptation thereby treating the malocclusions.

21 Claims, 6 Drawing Sheets

U.S. PATENT DOCUMENTS

| | | | |
|---|---|---|---|
| 5,645,424 A | 7/1997 | Collins, Jr. | |
| 5,678,990 A | 10/1997 | Rosenberg | |
| 5,697,781 A | 12/1997 | Ellingson | |
| 5,711,667 A | 1/1998 | Vogt | |
| 5,738,514 A | 4/1998 | DeVincenzo et al. | |
| 5,829,975 A | 11/1998 | Gold | |
| 5,848,891 A | 12/1998 | Eckhart et al. | |
| 5,853,291 A | 12/1998 | DeVincenzo et al. | |
| 5,879,157 A | 3/1999 | Scheu | |
| 5,944,518 A | 8/1999 | Sabbagh | |
| 5,964,588 A * | 10/1999 | Cleary | 433/19 |
| 5,980,247 A | 11/1999 | Cleary | |
| 6,099,304 A | 8/2000 | Carter | |
| 6,113,390 A | 9/2000 | Sirney et al. | |
| 6,234,792 B1 | 5/2001 | DeVincenzo | |
| 6,244,862 B1 | 6/2001 | Hanks | |
| 6,254,384 B1 | 7/2001 | Rosenberg | |
| 6,273,713 B1 | 8/2001 | Liou | |
| 6,328,562 B1 | 12/2001 | Sirney et al. | |
| 6,334,771 B1 | 1/2002 | Liou | |
| 6,361,315 B1 | 3/2002 | Hanks | |
| 6,394,799 B1 | 5/2002 | Testa et al. | |
| 6,413,082 B2 | 7/2002 | Binder | |
| 6,558,160 B2 | 5/2003 | Schnaitter et al. | |
| 6,589,051 B2 | 7/2003 | Cleary | |
| 6,655,959 B2 | 12/2003 | Farzin-Nia et al. | |
| 6,719,557 B1 | 4/2004 | Williams | |
| 6,832,911 B2 | 12/2004 | Forster | |
| 6,913,460 B2 | 7/2005 | Cleary et al. | |
| 2001/0036615 A1 | 11/2001 | Binder | |
| 2002/0025502 A1 | 2/2002 | Williams | |
| 2002/0031741 A1 | 3/2002 | Williams | |
| 2002/0132207 A1 * | 9/2002 | Tuneberg | 433/19 |
| 2002/0172909 A1 | 11/2002 | Williams | |
| 2003/0069595 A1 * | 4/2003 | Phung et al. | 606/184 |
| 2003/0207226 A1 | 11/2003 | Forster | |
| 2003/0232301 A1 | 12/2003 | Cleary et al. | |
| 2004/0197725 A1 | 10/2004 | Lluch | |
| 2004/0219474 A1 | 11/2004 | Cleary | |

FOREIGN PATENT DOCUMENTS

FR     2 702 141     9/1994

OTHER PUBLICATIONS

Claudio Salvatore (Authorized Officer); International Preliminary Report on Patentability, dated Oct. 9, 2007; 11 pages; European Patent Office.

* cited by examiner

ORTHODONTIC DEVICE FOR TREATING MALOCCLUSIONS

CROSS REFERENCE TO RELATED APPLICATIONS

This application claims the benefit of U.S. Provisional Application Ser. No. 60/702,142 filed on Jul. 25, 2005, the disclosure of which is expressly incorporated by reference herein in its entirety.

TECHNICAL FIELD

The present invention relates generally orthodontic appliances, and more particularly to an orthodontic device for treating malocclusions.

BACKGROUND

Orthodontic treatment involves movement of malpositioned teeth to orthodontically correct positions. During treatment, small orthodontic appliances known as brackets are often connected to anterior, bicuspid, and molar teeth, and an archwire is placed in a slot of each bracket. The archwire forms a track to guide movement of the brackets and the associated teeth to desired positions for correct occlusion. Typically, the ends of the archwire are held by appliances known as buccal tubes that are secured to a patient's molar teeth. The brackets, archwires, and buccal tubes are commonly referred to as "braces."

The orthodontic treatment of some patients includes correcting the alignment of the upper dental arch, or maxillary jaw, with the lower dental arch, or mandible jaw. For example, certain patients have a condition referred to as a Class II malocclusion, or "overbite," where the lower dental arch is located an excessive distance in a rearward direction relative to the location of the upper dental arch when the jaws are closed. Other patients may have an opposite condition referred to as a Class III malocclusion, or "underbite," wherein the lower dental arch is located in a forward direction of its desired location relative to the position of the upper dental arch when the jaws are closed.

A number of approaches have been developed to treat Class II and Class III malocclusions. One of the most common approaches for treating a Class II malocclusion is to use an intra-oral orthodontic appliance known as a "Herbst" device. A conventional Herbst device is comprised of a sleeve and tube assembly. Typically, one component of the assembly is pivotally secured to a molar tooth in the upper arch, while another component is pivotally secured to a bicuspid or anterior tooth in the lower arch, or a cantilever arm in the lower arch. Oftentimes, both the sleeve and tube components are pivotally secured to an archwire, bracket, cap, or other orthodontic appliance associated with a particular tooth. Such a Herbst device is shown in U.S. Pat. No. 3,798,773 (1973), issued to Northcutt.

Herbst devices operate by forcing the lower arch into a desired occlusion position when the mouth is opened and closed. In other words, the Herbst devices prevent a patient from comfortably closing his or her mouth unless the lower arch is physically repositioned forward. If the arches are not repositioned, the sleeve of the Herbst device impacts a portion of the tube or an attachment connected to the tube so as to create a hard, fixed "stop" that is uncomfortable for the patient. To compensate for this uncomfortable stop the patient repositions their lower jaw forward. Eventually, the patient experiences muscular adaptation based upon a learned response such that the jaws begin to naturally close with the proper occlusion. Because Herbst devices were first developed in the early 1900's, their safety and reliability have been well documented.

Although Herbst devices have generally proven to be successful products, there are several concerns that limit their appeal and effectiveness. For example, Herbst devices are typically designed with long and stiff assemblies in order to withstand the significant forces exerted by the muscles of mastication. In addition to making the devices more noticeable within a patient's mouth, these large assemblies often create discomfort near the front of the mouth. Cheek muscles are relatively tighter around the anterior teeth than the posterior teeth and thus become easily irritated from tightly rubbing against the Herbst device.

Additionally, the anterior teeth have a tendency to flare or tip forward when they are connected to a Herbst device. While a conventional Herbst device may be used to correct a malocclusion at the same time that archwires and brackets are used to prevent this tipping, there are several significant challenges with doing so. Specifically, when the Herbst device extends from a molar on the upper arch to a bicuspid tooth or cantilever arm on the lower arch, the sleeve and tube assembly obstructs access to a large number of teeth. This obstruction makes it extremely difficult for practitioners to bond brackets to those teeth. Although some practitioners have attempted to circumvent this problem by welding extra parts onto the Herbst device or by placing the brackets in unusual positions, none of these ad-hoc approaches have proven to be a suitable solution.

As a result, many practitioners prefer to perform different treatment methodologies at different times. For example, a Herbst device may be used to correct a malocclusion prior to installing brackets for repositioning teeth. This separate treatment is undesirable to both the patient and practitioner because it not only increases the overall time that the patient must wear orthodontic appliances, but also increases the number of orthodontic modifications required to control the tipping of the anterior teeth.

For all these reasons, several attempts have been made to develop other suitable devices for correcting malocclusions. More specifically, several attempts have been made to develop a smaller intra-oral device that connects to the posterior teeth of a patient. As discussed above, the patient's cheek muscles are more relaxed at this rearward location in the mouth. Additionally, posterior teeth such as molars provide a good anchoring location for applying forces to move one jaw relative to the other jaw because of the relatively large size of their roots.

One such device is disclosed in U.S. Pat. No. 5,848,891 (1998), issued to Eckhart et al. and assigned to the Assignee of the present invention. The Eckhart device includes a first member mounted to a molar in the upper arch and a second member mounted to a molar in the lower arch. A buccally extending projection on the second member strikes an obstruction element on the first member when the lower jaw is closed in an uncorrected position. The obstruction element and buccally extending projection prevent complete closure of the upper and lower jaws unless the mandible is advanced sufficiently forward to enable the buccally extending projection to clear the obstruction element. Although such a disconnected system is relatively compact and does not interfere with braces or other orthodontic components, the contact between the obstruction element and the buccally extending projection provides only a limited range of correction. Furthermore, if the obstruction element and buccally extending projection do not make proper contact, these components may become engaged together and lock the upper and lower jaws.

Another type of intra-oral orthodontic device to treat Class II malocclusions includes one or more linkages having pivotal connections. These devices typically have a Z-shaped configuration and often incorporate a spring element to create a light, continuous force that enhances molar distalization. For example, U.S. Pat. No. 5,645,424 (1997), issued to Collins, Jr., discloses a central linkage having outer arms pivotally connected to the ends thereof. The outer arms are adapted to engage respective tubes on the molar teeth of the upper and lower dental arches. U.S. Pat. No. 5,980,247 (1999), issued to Cleary, discloses a related device having two linkages and three pivotal connections. U.S. Pat. No. 4,382,783 (1983), issued to Rosenberg, discloses a device having a configuration somewhat similar to the device of Cleary except that one of the linkages is a telescopic rod.

While the above-described devices have the advantages of a molar-to-molar connection, the increased number of parts and pivotal connections typically makes them more prone to breakage due to mastication forces. Additionally, many practitioners are hesitant to install such devices because their configurations differ significantly from traditional Herbst devices and therefore lack the extensive historical data and experience associated with traditional Herbst devices.

As can be appreciated, there is a need in the orthodontic art for improved devices for repositioning the jaws of patient with a Class II malocclusion. Devices are needed that function reliably and efficiently and yet are not prone to breakage or likely to cause adjacent orthodontic components to be detached from the associated teeth.

SUMMARY

One embodiment is an orthodontic device for positioning the lower dental arch of a patient relative to the upper dental arch. The device includes a telescoping rod defining a longitudinal axis and including at least two substantially coaxial sections. The telescoping rod also includes a first end adapted to be mounted to a molar tooth on the upper arch and a second end adapted to be mounted to a molar tooth on the lower arch. The coaxial sections are adapted to move relative to each other along the longitudinal axis between a first position wherein the upper and lower arches are closed and a second position wherein the upper and lower arches are opened.

Another embodiment is a method of positioning the lower dental arch of a patient relative to the upper dental arch. The method includes pivotally coupling a first end of a telescoping rod to a molar in the lower dental arch. The method further includes pivotally coupling a second end of a telescoping rod to a molar in the upper dental arch.

Another embodiment is an orthodontic device for positioning the lower dental arch of a patient relative to the upper dental arch. The device includes a telescoping rod assembly having four or more sections and having a first end adapted to be mounted to a molar tooth on the upper arch and a second end adapted to be mounted to a molar tooth on the lower arch.

Another embodiment is an orthodontic device for positioning the lower dental arch of a patient relative to the upper dental arch using a linkage. The linkage consists of a telescoping rod having a first end and a second end. The linkage also has a first attachment member rigidly attached to the first end. The first attachment member is adapted to be mounted to a molar tooth on the upper dental arch. A second attachment member is rigidly attached to the second end. The second attachment member is adapted to be mounted to a molar tooth on the lower dental arch.

Yet another embodiment is an orthodontic device for positioning the lower dental arch of a patient relative to the upper dental arch. The lower dental arch moves relative to the upper dental arch between an open position and a closed position. The device includes a telescoping rod having a longitudinal axis and a first end adapted to be mounted to a molar tooth on the upper arch and a second end adapted to be mounted to a molar tooth on the lower arch. The telescoping rod has a first length when the upper and lower dental arches are in the closed position and a second length when the upper and lower dental arches are in the open position. The telescoping rod moves along the longitudinal axis between the first and second lengths.

An additional embodiment is an orthodontic device for positioning the lower dental arch of a patient relative to the upper dental arch. The device includes a rod defining a longitudinal axis and having a first end adapted to be mounted to a molar tooth on the upper arch and a second end adapted to be mounted to a molar tooth on the lower arch. The device also includes a first attachment member coupled to the rod and adapted to pivotally couple said first end of the rod with the molar tooth on the upper arch. In addition the device includes a second attachment member coupled to the rod and adapted to pivotally couple said second end of the rod with the molar on the lower arch. The distance between the center of the first attachment member and the second attachment member is less than about 12 millimeters. The ends are adapted to move relative to each other along the longitudinal axis between a first position wherein the upper and lower arches are in a closed position and a second position wherein the upper and lower arches are in an opened position.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION OF ILLUSTRATIVE EMBODIMENTS

Figure 1:
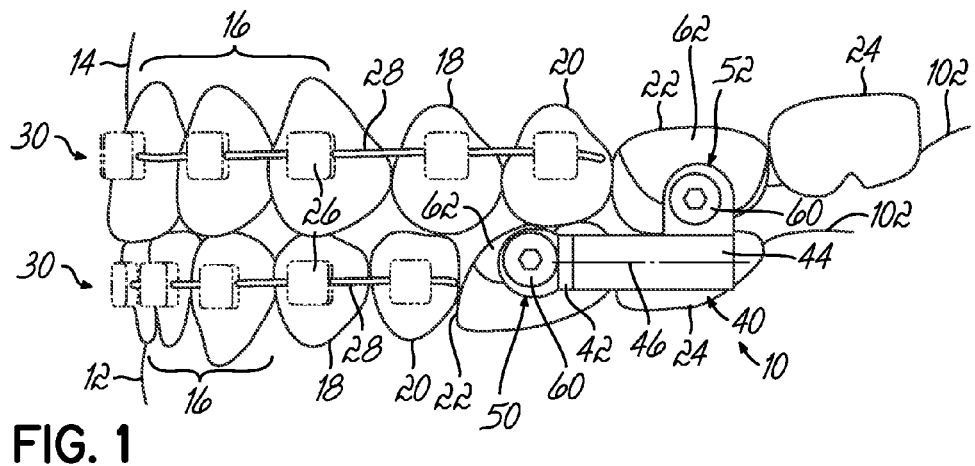
FIG. 1 is a side view of an orthodontic device according to an embodiment of the present invention, the orthodontic device being shown with an upper dental arch and lower dental arch of a patient in a closed position.

With reference to FIGS. 1 through 4, an orthodontic device 10 according to an embodiment of the invention is shown. The orthodontic device 10 is generally designed to reposition a lower dental arch or mandible jaw 12, relative to an upper dental arch or maxillary jaw 14. By way of background, the upper arch 14 and lower arch 12 each include a set of anterior teeth 16, first and second bicuspid teeth 18, 20, and first and second molars 22, 24. A bracket 26 is secured to each tooth and an archwire 28 extends through the brackets 26 in order to provide each dental arch with a set of braces 30. The braces 30 help guide the teeth into the correct positions for proper occlusion.

As shown in the figures, the orthodontic device 10 comprises a telescopic rod 40 having a first end 42 and a second end 44 aligned along an axis 46. A first attachment member 50 associated with the first end 42 is generally aligned along the axis 46 and adapted to pivotally couple the telescopic rod 40 to the first molar 22 on the lower dental arch 12. Meanwhile, a second attachment member 52 associated with the second end 44 is generally offset from the axis 46 and adapted to pivotally couple the telescopic rod 40 to the first molar 22 on the upper dental arch 14.

Those skilled in the art will appreciate that there are a number of ways to pivotally couple the telescopic rod 40 to the molars 22. For example, the first and second attachment members 50, 52 may each include an eyelet 58 for receiving a fastening member 60. The fastening members 60 may each be secured to a cap or band 62, archwire 28, bracket 26, and/or buccal tube (not shown) or other components on the associated first molar 22. In the embodiment shown in the figures, the fastening members 60 are screws that are adapted to engage a threaded bore (not shown) provided on each molar cap 62. Preferably, the threaded bore is provided in the middle of each molar cap 62. But the location of the bore may be altered as necessary to achieve a molar-to-molar connection. The screws 60 allow the first and second attachment members 50, 52 to pivot as the patient's jaws are opened and closed.

Figure 2:
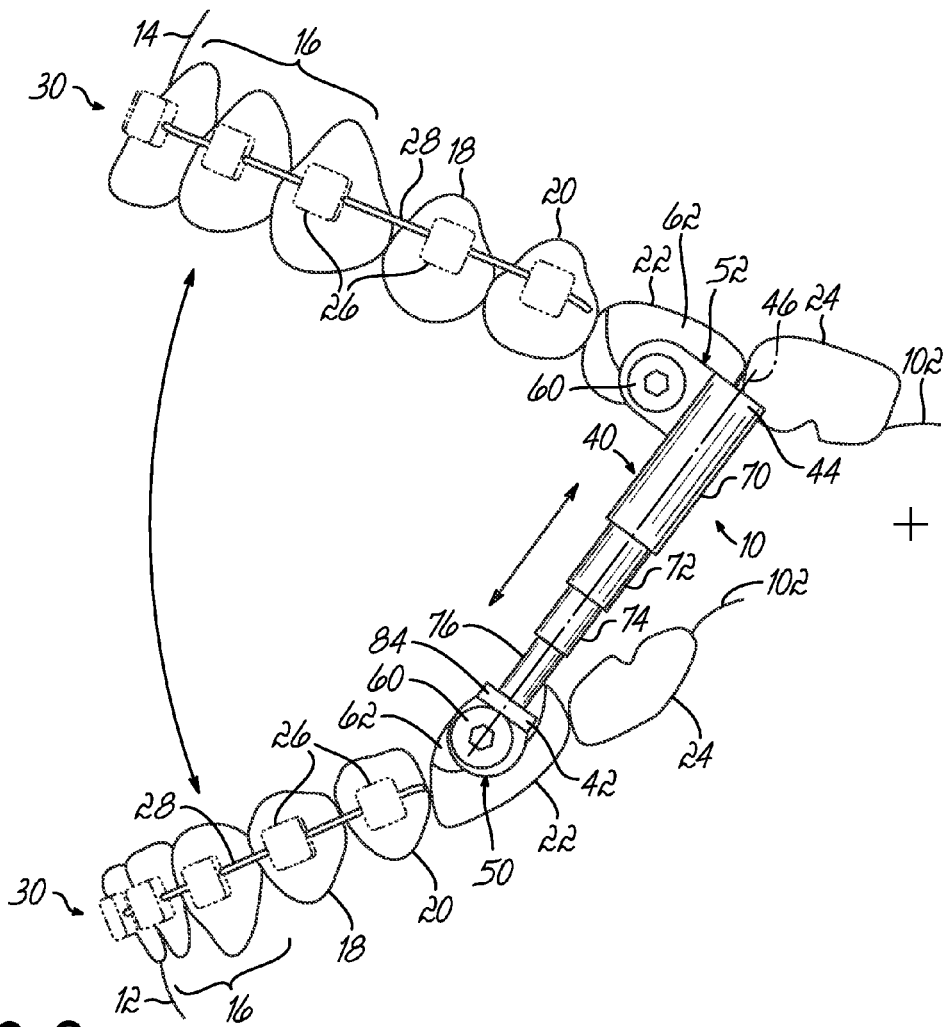
FIG. 2 is a side view similar to FIG. 1 showing the orthodontic device with the upper dental arch and lower dental arch in an open position.
Figure 3:
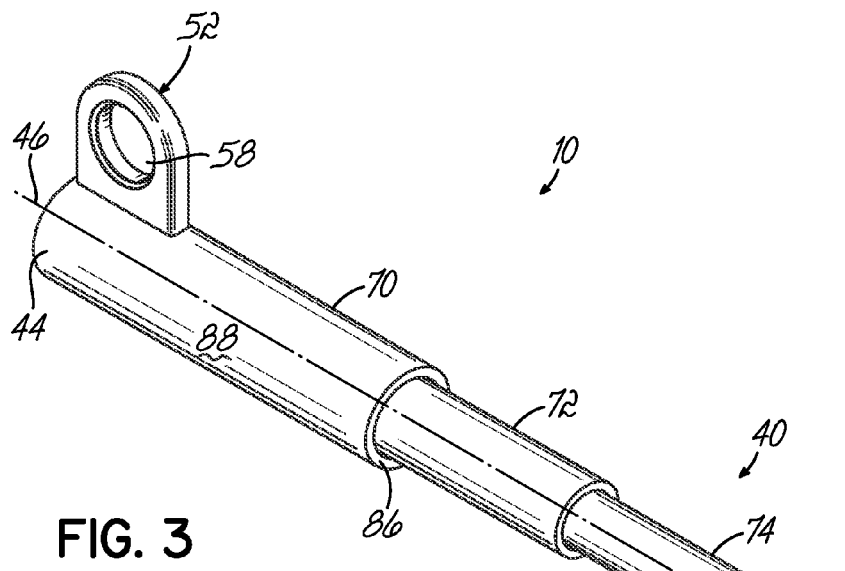
FIG. 3 is a perspective view of the orthodontic device shown in FIG. 1.

As shown in FIGS. 2 and 3, the telescopic rod 40 includes a plurality of tubes adapted to slide relative to each other along the axis 46 such that the telescopic rod 40 has an adjustable length. In one embodiment, the telescopic rod 40 includes four sections: an outer tube 70, a first intermediate tube 72 adapted to be slidably received in the outer tube 70, a second intermediate tube 74 adapted to be slidably received in the first intermediate tube 72, and an inner tube or rod 76 adapted to be slidably received in the second intermediate tube 74. Accordingly, the outer tube 70, first intermediate tube 72, and second intermediate tube 74 each include at least a hollow portion, whereas the inner tube 76 may or may not include a hollow portion. The sections of the telescopic rod 40 can be formed from different materials, such as metal, plastic, ceramic or other materials readily apparent to those skilled in this art. In addition, a coating can be applied over the different sections, such as Teflon® (PTFE) or other low friction material readily apparent to those skilled in this art. The advantages in coating the sections of the telescopic rod 40 include making the sections slide easier for improved comfort, reduced section binding and preventing potential breakage of the orthodontic device 10.

The inner tube 76 is coupled to a disc-shape portion 84 of the first attachment member 50. The disc-shaped portion 84 is adapted to contact an end surface 86 of the outer tube 70 and thus acts as a "stop" to prevent the inner tube 76 from extending through the other tubes when the dental arches are in a closed position (FIG. 1). The second attachment member 52 is coupled to an outer cylindrical surface 88 of the outer tube 70 adjacent second end 44. Both the first and second attachment members 50, 52 may be integrally formed with the respective tube to which they are coupled in order to simplify the construction of the orthodontic device 10. Also, note that the telescopic rod 40 may be arranged in other manners, such as with the second attachment member 52 coupled to an inner tube and the first attachment member 50 coupled to an outer tube.

Figure 4:
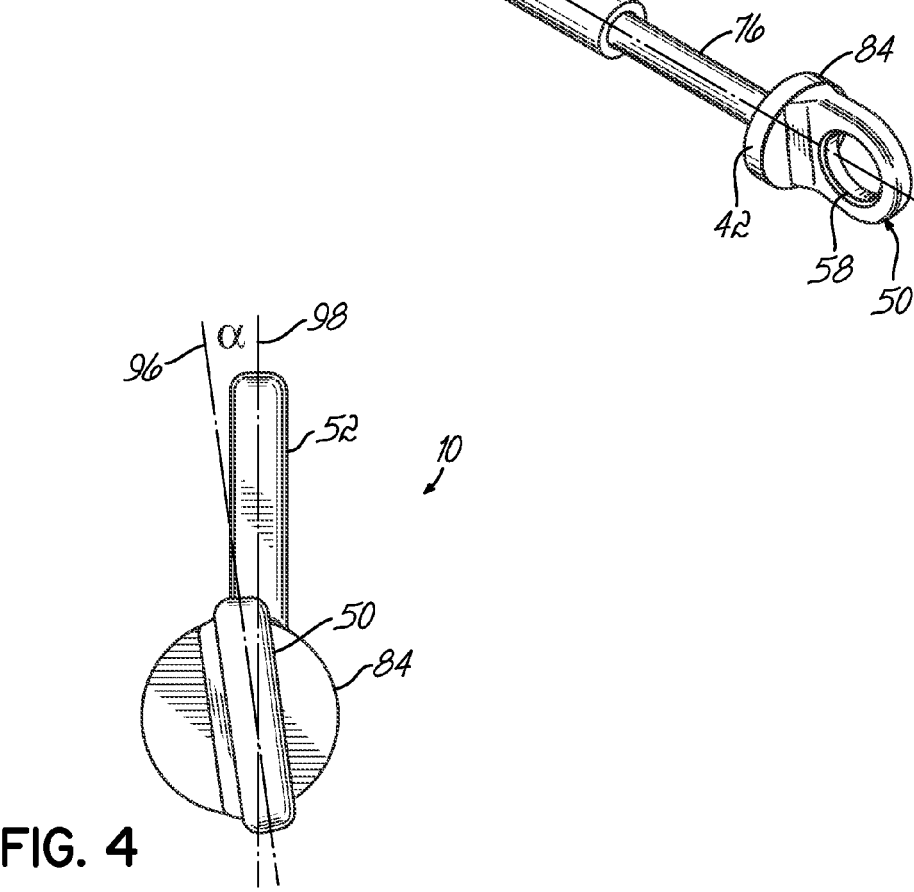
FIG. 4 is a frontal view of the orthodontic device shown in FIG. 1.

With reference to FIG. 4, the first attachment member 50 is generally aligned in a plane 96 and the second attachment member 52 is generally aligned in a plane 98. The planes may be angled relative to each other, for example, at an angle α between approximately 7 and 18 degrees. In this manner, the first attachment member 50 is not directly aligned with the second attachment member 52. Such an arrangement facilitates coupling the first and second attachment members 50, 52 to the respective dental arches 12, 14. In order to achieve this orientation, at least one of the telescopic rod sections 70, 72, 74, 76 may be adapted to rotate about the axis 46 relative to the other sections 70, 72, 74, 76. Alternatively, the telescopic rod sections 70, 72, 74, 76 may be initially assembled with this orientation and prevented from rotating about the axis 46.

The operation of the orthodontic device 10 will now be described in further detail. FIG. 1 shows the upper arch 14 and lower arch 12 in a normal, closed position. Because of the offset of the second attachment member 52, the axis 46 of the telescopic rod 40 is aligned generally parallel to the occlusal plane. Such an arrangement helps maximize the horizontal force vectors exerted by the orthodontic device 10. In other words, if a patient attempts to move the lower arch 12 in a rearward direction when the jaws are closed, the telescopic rod 14 will exert a horizontal force against the lower arch 12 to counteract this attempted movement. The offset of the second attachment member 52 may also be designed to align the telescopic rod 40 with the gum line.

As shown in FIG. 2, the sections 70, 72, 74, 76 of the telescopic rod 40 slide relative to each other along the axis 46, and first and second attachment members 50, 52 pivot about the screws 60 in order to allow the patient's jaws to move into an open position. Because the telescopic rod 40 includes four slidable sections 70, 72, 74, 76, the range of expansion of the jaws is greatly enhanced. For example, the orthodontic device 10 preferably has a length of approximately 12 mm in the closed position and a length of at least approximately 34 mm in the open position, with the length being defined as the distance between the respective eyelets 58 of the first and second attachment members 50, 52 in a direction along the axis 46. Such an arrangement ensures that the orthodontic device 10 is able to maintain a molar-to-molar connection without significantly interfering with chewing, yawning, and other movements that require full expansion of the telescopic part of the appliance.

When the patient attempts to close his or her jaws, the outer tube 70 will slide over the other sections 72, 74, 76 of the telescopic rod 40 until the end surface 86 contacts the disc-shaped portion 84 of the first attachment member 50. If the lower arch 12 is positioned an excessive distance in a rearward direction relative to the location of the upper arch 14, the orthodontic device 10 will be angled relative to the occlusal plane and prevent the jaws from closing completely. Thus, in order to mover the upper arch 14 and lower arch 12 into a closed position, the patient must force the lower arch 12 in a forward direction until the telescopic rod 40 is aligned substantially parallel with the occlusal plane. As with conventional Herbst devices, eventually the patient will experience muscular adaptation based upon this forced response and begin closing his or her jaws with the proper occlusion.

The embodiment shown in FIGS. 1 through 4 is particularly suited for patients having a fully erupted second molar 24. In these patients, contact between the second end 44 of the telescopic rod 40 and tissue 102 or the descending portion of the ramus is less of a concern. As shown in FIG. 1, the second attachment member 52 may extend substantially orthogonally from the outer tube 70 so that the second end 44 overlaps the second molar 24 on the lower dental arch 12. The fully erupted second molar 24 prevents contact with the tissue 102 and avoids the patient discomfort associated with such contact.

Figure 5:
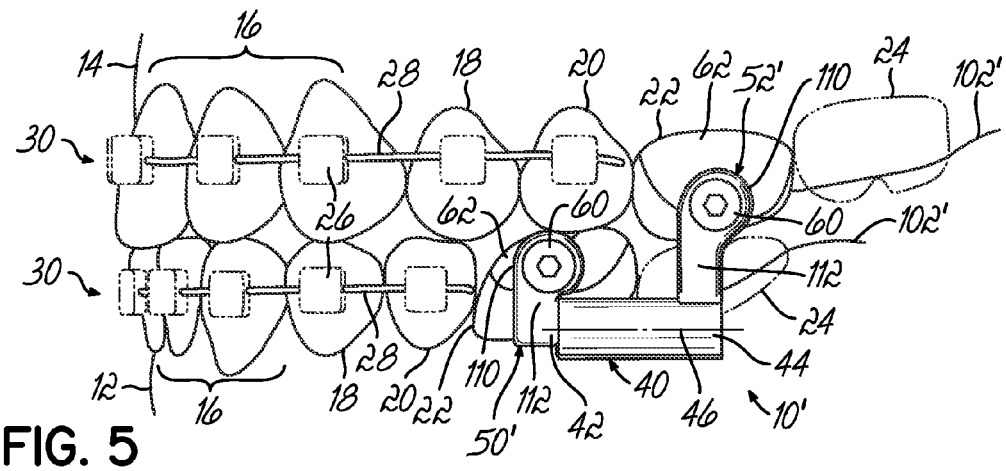
FIG. 5 is a side view similar to FIG. 1 showing an orthodontic device according to an alternative embodiment of the invention in a closed position.
Figure 6:
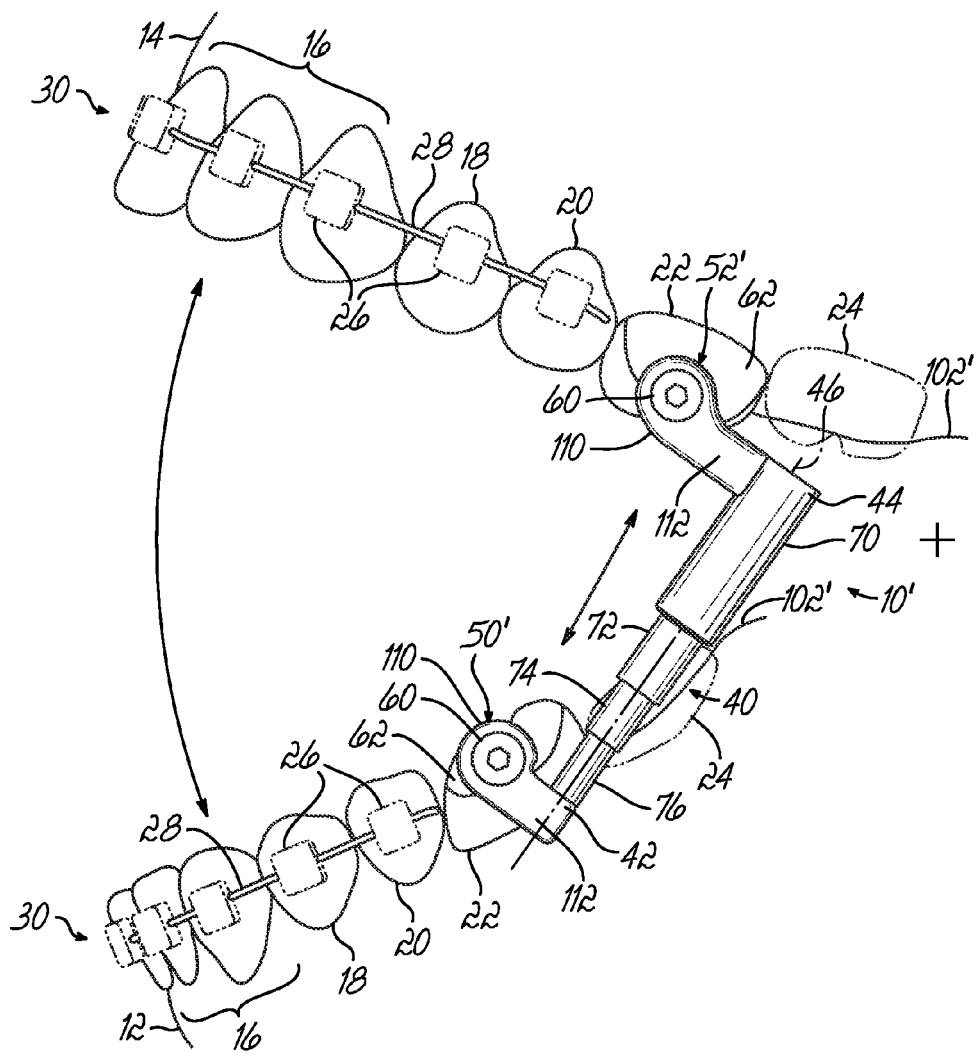
FIG. 6 is a side view similar to FIG. 5 showing the orthodontic device with the upper dental arch and lower dental arch in an open position.
Figure 7:
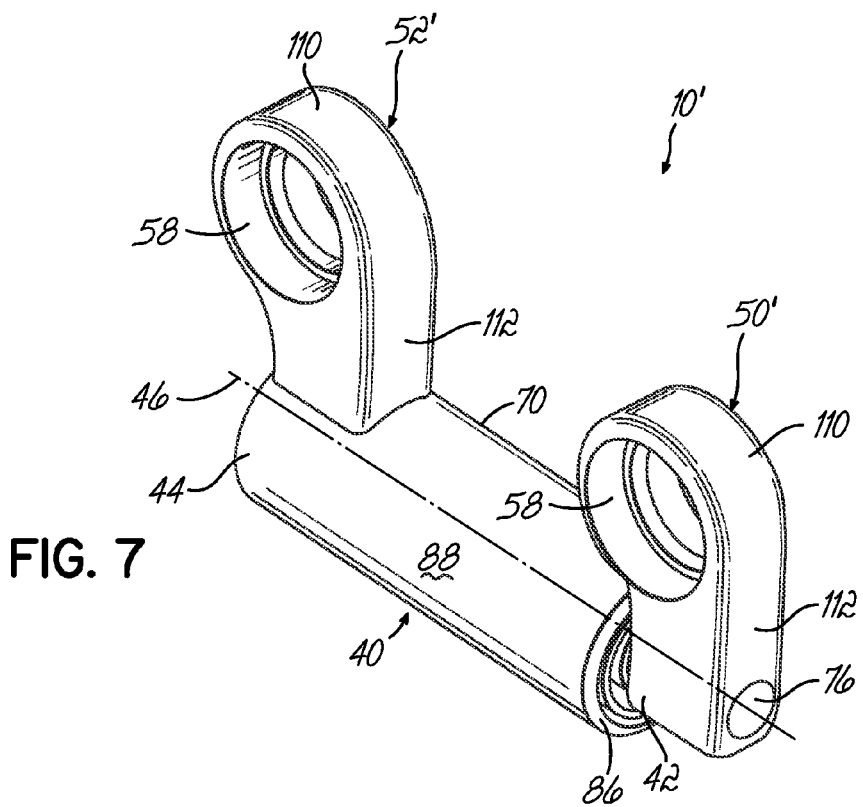
FIG. 7 is a perspective view of the orthodontic device shown in FIG. 5.
Figure 10:
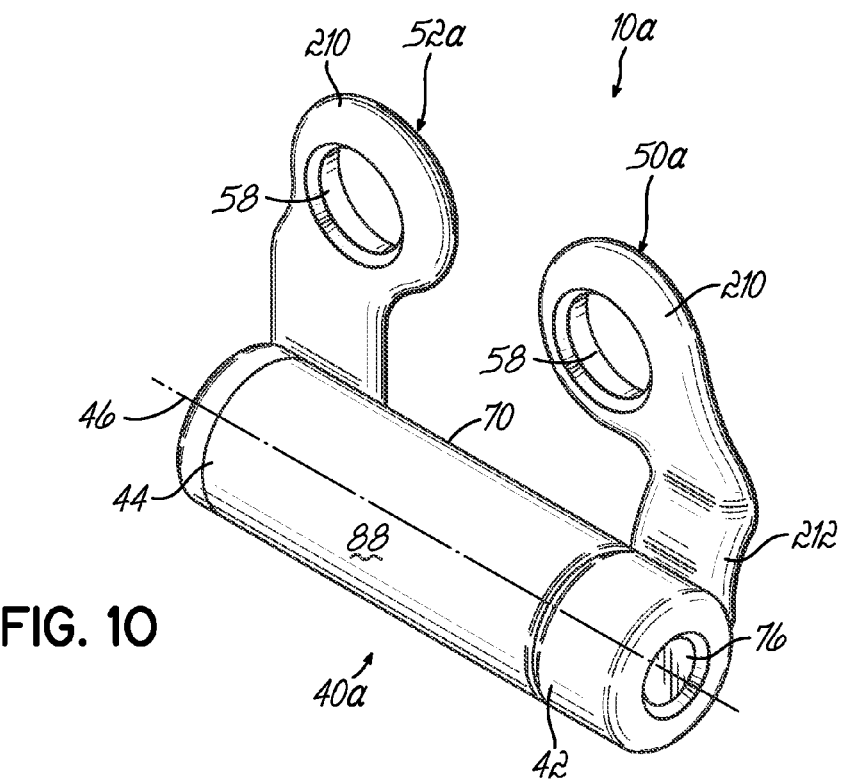
FIG. 10 is a perspective view of the orthodontic device shown in FIG. 8.

FIGS. 5 through 7 illustrate an alternative embodiment of the invention that is particularly suited for patients who may not have a fully erupted second molar 24. Like reference numbers are used in the figures to refer to like elements from the embodiment discussed above, while like reference numbers with prime marks (') represent corresponding elements that have been slightly modified as will be apparent from the description, the figures, or both. Soft tissue 102' is positioned behind the first molar 22 of the upper and lower arches 12, 14 in place of the second molar 24 (FIGS. 1-2).

As shown in FIGS. 5 through 7, the first and second attachment members 50', 52' have a different design than the first and second attachment members 50, 52. In this embodiment, both the first and second attachment members 50', 52' are offset from the axis 46. The second attachment member 52' has an offset greater than the first attachment member 50' so that the telescopic rod 40 remains substantially parallel to the occlusal plane when the upper arch 14 and lower arch 12 are in a closed position (FIG. 5). The offsets may also be designed such that the telescopic rod 40 is substantially parallel to the gum line.

Preferably, the first and second attachment members 50', 52' each include a round portion 110 surrounding the eyelet 58 and a generally straight extension portion 112 coupled to the telescopic rod 40. The extension portions 112 are oriented substantially orthogonal to the axis 46, while the round portions 110 are slightly offset in a rearward or distal direction relative to the extension portion 112. Such a P-shaped configuration enables the telescopic rod 40 to maintain a molar-to-molar connection yet be positioned further towards the anterior and bicuspid teeth than the embodiment shown in FIGS. 1 through 4.

The orthodontic device 10' shown in FIGS. 5 through 7 operates under the same general principles that were discussed with respect to the embodiment shown in FIGS. 1 through 4. However, due to the offset of the first attachment member 50', the increased offset of the second attachment member 52', and the forward positioning created by the P-shaped configuration of both the first and second attachment members 50', 52', the second end 44 of the telescopic rod 40 is spaced further away from the tissue 102'. This not only moves the device forward (mesially) in the mouth where cheek tissue is relatively looser, but when the jaws are opened and closed, the orthodontic device 10' shown in FIGS. 5 through 7 reduces the possibility of contact of the device with the soft tissue 102' and other structures of the mouth including the descending portion of the ramus.

FIGS. 8 through 11 illustrate a device 10a according to an alternative embodiment of the invention that is particularly suited for minimizing the distance between attachment members. Minimizing the distance between the attachment members ensures molar-to-molar attachment with efficient use of space. The design is particularly advantageous for an individual with smaller teeth where the distance between the distal end of the molar tooth on the upper jaw and the mesial end of the molar tooth on the lower jaw is reduced, such as being less than 12 millimeters, and therefore would not accommodate the entire telescoping rod 40a in its shortest configuration. In FIGS. 8 through 11, like reference numbers are used in the figures to refer to like elements from the embodiment discussed above, while like reference numbers with the letter "a" as a suffix represent corresponding elements that have been slightly modified as will be apparent from the description, the figures, or both.

Figure 8:
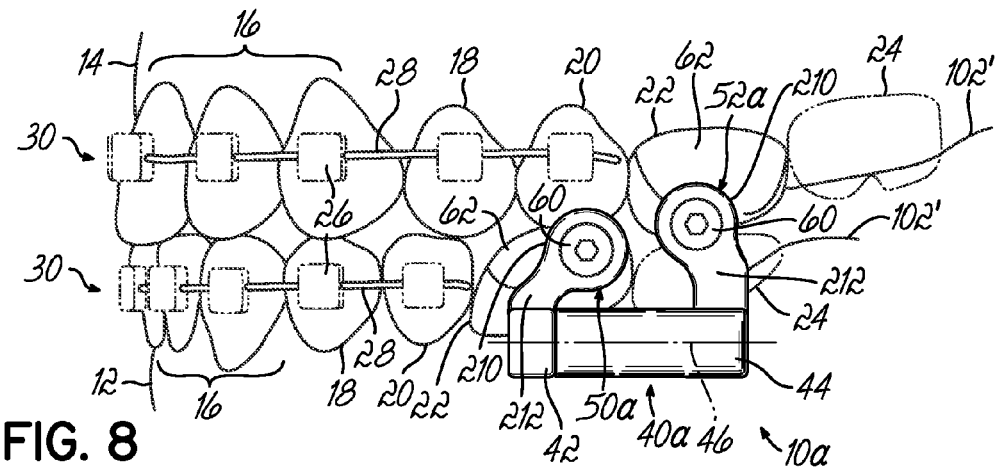
FIG. 8 is a side view similar to FIGS. 1 and 5 showing an orthodontic device according to another alternative embodiment of the invention in a closed position.
Figure 9:
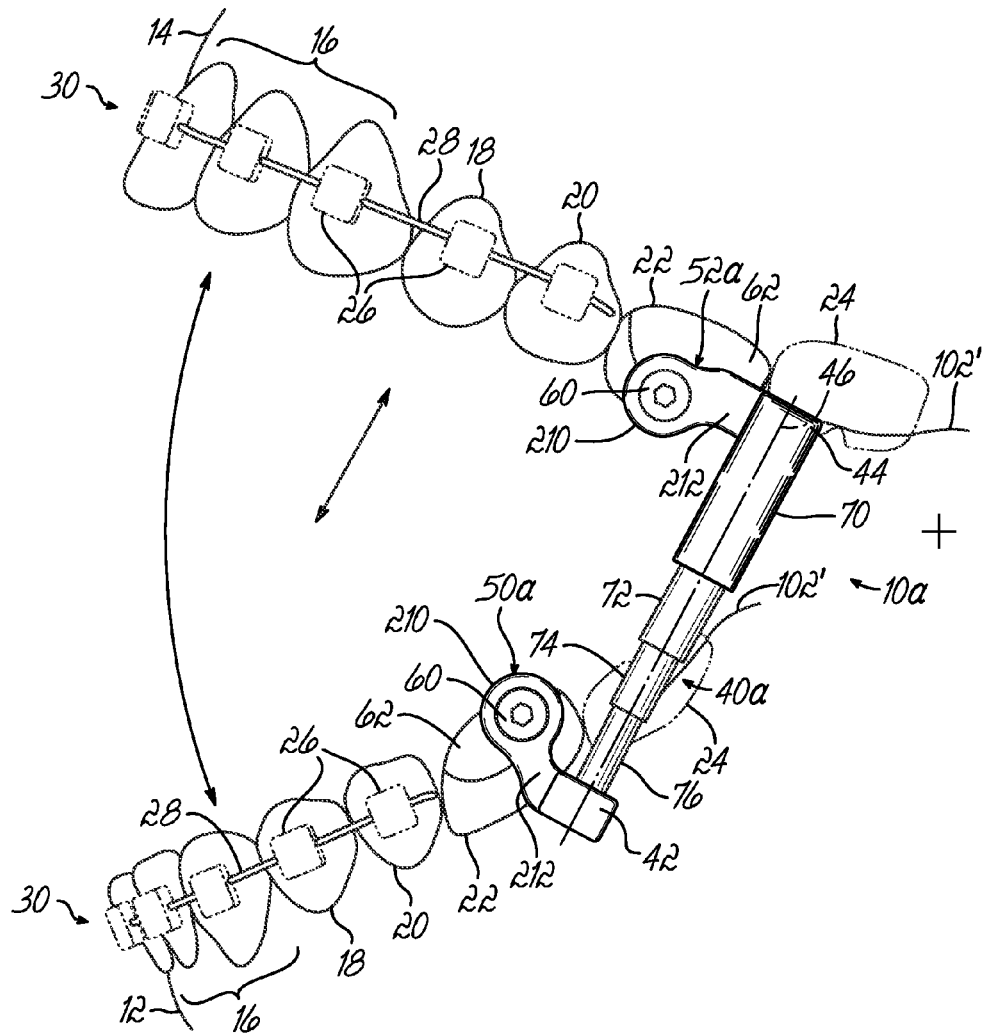
FIG. 9 is a side view similar to FIG. 8 showing the orthodontic device with the upper dental arch and lower dental arch in an open position.

As shown in FIGS. 8 through 11, the first and second attachment members 50a, 52a have a different design than the attachment members 50, 52, 50', 52' illustrated in FIGS. 1-7. The attachment members 50a, 52a are positioned on the ends 42, 44, as in the other embodiments, but the offsets and positioning of the eyelets 58 are different. In this embodiment, both the first and second attachment members 50a, 52a are offset from the axis 46 in a first and a second direction. Both attachment members 50a, 52a are offset from the axis 46 by extending away from the axis 46 in a first direction generally orthogonal to the axis 46 and generally in a gingival-occlusal direction when the orthodontic device 10a is positioned inside of the mouth. The attachment members 50a, 52a are also offset from the axis 46 in a second direction generally orthogonal to the axis 46 and the first direction. Accordingly, the second offset is generally along the labial-lingual direction. The result is an orthodontic device 10a that has attachment members 50a, 52a that extend in an upward direction towards the arch 14 and that are positioned on the side of the device 10a that is proximate to the arches 12, 14 (see FIG. 10). These offsets enable close positioning of the eyelets 58 to the bands 62 on the molar teeth. The second attachment member 52a has an offset greater than the first attachment member 50a in the first direction so that the telescopic rod 40a remains substantially parallel to the occlusal plane when the upper arch 14 and lower arch 12 are in a closed position (FIG. 8). The offsets in the first direction may be designed such that the telescopic rod 40a is substantially parallel to the gum line. In the second direction, the offset of the second attachment member 52a may be greater than the offset of the first attachment member 50a to match the offset of the outer surface of the molar teeth when in proper occlusion.

Preferably, the first and second attachment members 50a, 52a each include a round portion 210 surrounding the eyelet 58 and a generally straight extension portion 212 coupled to the telescopic rod 40a. The extension portions 212 extend in an occlusal-gingival direction. The round portions 210 converge inwardly from the straight portions 212 towards each other and the center of the outer cylindrical surface 88. Such a configuration enables the telescopic rod 40 to maintain a molar-to-molar connection and greatly minimize the distance between the eyelets 58 keeping the size of the orthodontic device 10a small.

Figure 11:
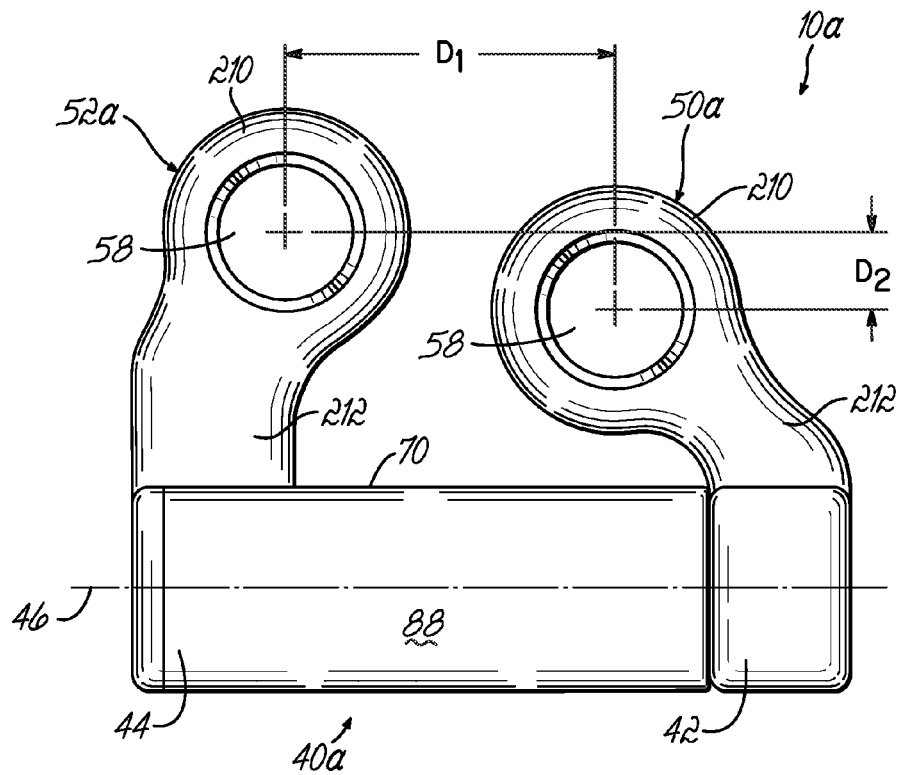
FIG. 11 is a side elevational view of the orthodontic device of FIG. 10.

FIG. 11 illustrates that the distance $D_1$ between the eyelets 58 of the attachment members 50a, 52a along axis 46 is shorter than the length of the telescopic rod 40. Shortening the distance between the eyelets 58 facilitates attachment when a patient has small molars. The entire length of the telescopic rod 40, such as 12 millimeters, fits inside the mouth even if, for example, the distance between the molars is only 10 millimeters. The smaller distance $D_1$ between the eyelets 58 will accommodate these small molars. In addition, the distance $D_2$ between the location of a first center 214 and a second center 216 of the eyelets 58 of the first and second attachment members 50a, 52a in the first direction keeps the telescopic rod 40a substantially parallel to the occlusal plane when the upper arch 14 and lower arch 12 are in a closed position, as in FIG. 8. FIG. 11 also illustrates that the first attachment member 50a is offset towards the second end 44 of the telescopic rod 40a and the second attachment member 52a is offset towards the first end 42 of the telescopic rod 40a. The centers 214, 216 are thereby positioned closer together by these offsets. The positioning of these centers 214, 216 in such a manner moves the orthodontic device 10a forward (mesially) along the arches 12, 14 improving comfort since the cheek loosens mesially and there is less contact with the descending portion of the ramus. The orientation of the centers 214, 216 also keeps the telescopic rod 40a substantially parallel to the occlusal plane and minimizes the distance between the centers 214, 216.

The orthodontic device 10a shown in FIGS. 8 through 11 operates under the same general principles that were discussed with respect to the embodiments shown in FIGS. 1 through 7. Advantageously, however, the dual offsets of the attachment members 50a, 52a and close positioning of the eyelets 58 by the configuration of both the first and second attachment members 50a, 52a, reduces the distance between attachment members 50a, 52a and the eyelets 58. Thus, the total length of the orthodontic device 10a is lessened increasing the ease of implantation and operation even in patients with small molars.

Figure 12:
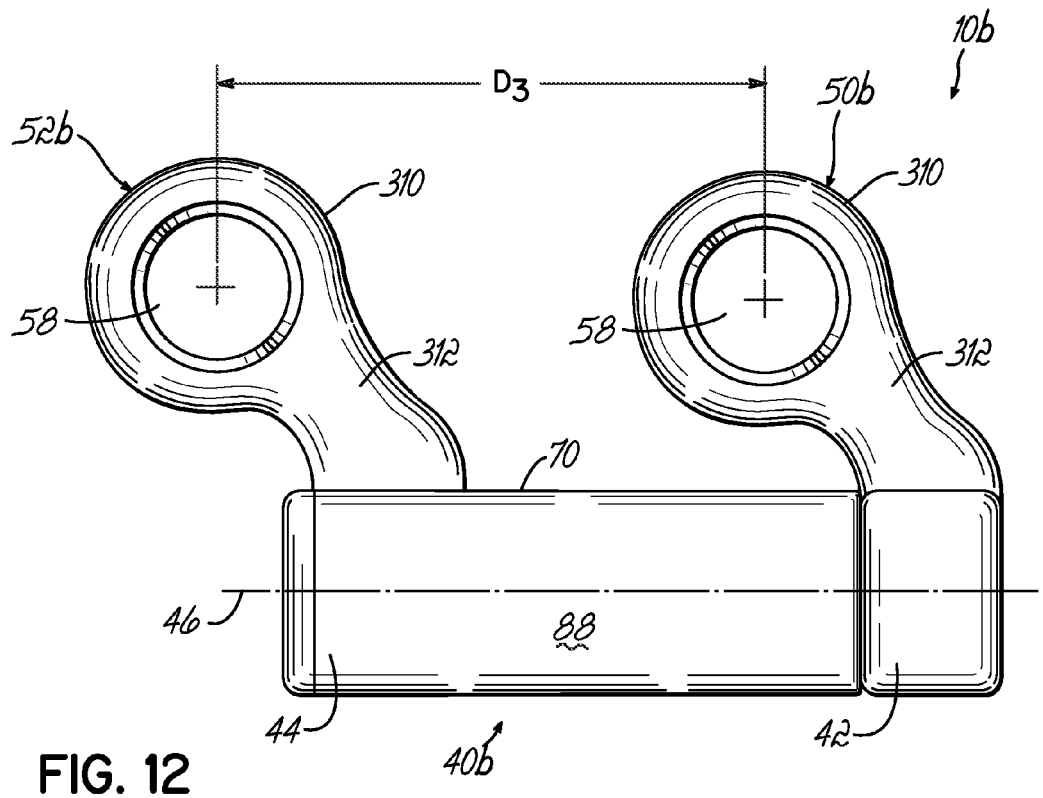
FIG. 12 is a side elevational view of a further alternative embodiment of the invention.

FIG. 12 illustrates an orthodontic device 10b similar to the orthodontic device 10a shown in FIGS. 8 through 11 and generally operates under the same general principles. In FIG. 12, like reference numbers are used in the figures to refer to like elements from the embodiment discussed above, while like reference numbers with the letter "b" as a suffix represent corresponding elements that have been slightly modified as will be apparent from the description, the figures, or both. The orthodontic device 10b has attachment members 50b and 52b that are very similar to the attachment members 50a and 52a. The first attachment member 50b, however, is offset away from the first end 42 instead of towards the second end 44. In addition, the extension portion 312 for the first attachment member 50b has a different configuration. The distance $D_3$ is less than the distance between the centers of the apertures 58 illustrated in FIG. 7. Therefore, for example, the distance $D_3$ can be less than about 12 millimeters. In another embodiment, the distance can be less than or equal to about 10 millimeters. Accordingly, a offset configuration similar to the configuration illustrated in FIG. 7 can be applied to smaller molars.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. The various features of the different embodiments may be combined in any manner so as to be suitable and desirable for a given patient and/or condition. Accordingly, departures may be made from such details without departing from the scope or spirit of Applicants' general inventive concept.

What is claimed is:

1. An orthodontic device for positioning the lower dental arch of a patient relative to the upper dental arch, the lower arch including a lower molar adapted to receive a first fastener, the upper arch including an upper molar adapted to receive a second fastener, the orthodontic device comprising:
a telescoping rod defining a longitudinal axis and including at least two substantially coaxial sections movable relative to each other along said longitudinal axis between a first position wherein the upper and lower arches are closed and a second position wherein the upper and lower arches are open, said telescoping rod having a first end and a second end;
a first attachment member rigidly coupled to said first end of said telescoping rod and having a first eyelet adapted to receive the first fastener to couple said first end to the lower molar, said first attachment member offset from said longitudinal axis in a first direction generally orthogonal to said longitudinal axis and further offset from said first end in a second direction substantially parallel to said longitudinal axis, wherein the first direction generally corresponds to a gingival-occlusal direction and the second direction generally corresponds to a mesial-distal direction when the orthodontic device is installed in the patient's mouth; and
a second attachment member rigidly coupled to said second end of said telescoping rod and having a second eyelet adapted to receive the second fastener to couple said second end to the upper molar, said second attachment member offset from said longitudinal axis in the first direction and on the same side of said telescoping rod as said first attachment member;
wherein said first eyelet has a center offset from said longitudinal axis in the first direction by a first distance and said second eyelet has a center offset from said longitudinal axis in the first direction by a second distance, said second distance being greater than said first distance so that said telescoping rod is substantially parallel to an occlusal plane when in the first position.

2. The orthodontic device of claim 1 wherein said first attachment member is defined by a generally straight extension portion coupled to said telescoping rod and a round portion surrounding said first eyelet.

3. The orthodontic device of claim 1 wherein said first attachment member is offset in the second direction generally toward said second attachment member.

4. The orthodontic device of claim 2 wherein said generally straight extension portion of said first attachment member is generally aligned in a plane offset from said longitudinal axis in a third direction, wherein the third direction generally corresponds to a labial-lingual direction when the orthodontic device is installed in the patient's mouth.

5. The orthodontic device of claim 1 wherein said second attachment member is further offset from said second end in the second direction.

6. The orthodontic device of claim 5 wherein said second attachment member is defined by a generally straight extension portion coupled to said telescoping rod and a round portion surrounding said second eyelet.

7. The orthodontic device of claim 5 wherein said second attachment member is offset in the second direction generally toward said first attachment member.

8. The orthodontic device of claim 5 wherein said first attachment member is offset in the second direction generally toward said second attachment member.

9. The orthodontic device of claim 8 wherein said first and second attachment members are each defined by a generally straight extension portion coupled to said telescoping rod and a round portion offset surrounding said associated first or second eyelet, said generally straight extension portion of said first attachment member being generally aligned in a first plane offset from said longitudinal axis in a third direction, and said generally straight extension portion of said second attachment member being generally aligned in a second plane offset from said longitudinal axis in the third direction, wherein the third direction generally corresponds to a labial-lingual direction when the orthodontic device is installed in a patient's mouth.

10. The orthodontic device of claim 8 wherein said first and second eyelets each include a center, said center of said first eyelet being spaced apart from said center of said second eyelet by a first distance measured in a direction along said longitudinal axis, the first distance being less than about 10 mm when said telescoping rod is in the first position.

11. The orthodontic device of claim 1 wherein said first and second attachment members are configured so that said telescoping rod is substantially aligned with a gum line when in the first position.

12. The orthodontic device of claim 1 wherein said telescoping rod includes at least four substantially coaxial sections.

13. The orthodontic device of claim 1 wherein said first and second eyelets each include a center, said center of said first eyelet being spaced apart from said center of said second eyelet by a first distance measured in a direction along said longitudinal axis, the first distance being less than about 12 mm when said telescoping rod is in the first position.

14. The orthodontic device of claim 13 wherein the first distance is approximately 10 mm when said telescoping rod is in the first position.

15. The orthodontic device of claim 13 wherein the first distance is at least approximately 34 mm when said telescoping rod is in the second position.

16. The orthodontic device of claim 13 wherein said telescoping rod has a length measured from said first end to said second end, the first distance being less than the length of said telescoping rod.

17. The orthodontic device of claim 1 wherein said at least two substantially coaxial sections are coated with a low friction coating.

18. The orthodontic device of claim 1 wherein said first attachment member is generally aligned in a first plane and said second attachment member is generally aligned in a second plane, said first plane being positioned relative to said second plane so that an angle is formed therebetween.

19. The orthodontic device of claim 18 wherein said angle formed between said first and second planes is between approximately 7 and 18 degrees.

20. An orthodontic device for positioning the lower dental arch of a patient relative to the upper dental arch, the lower arch including a lower molar adapted to receive a first fastener, the upper arch including an upper molar adapted to receive a second fastener, the orthodontic device comprising:
    a telescoping rod defining a longitudinal axis and including at least two substantially coaxial sections movable relative to each other along said longitudinal axis between a first position wherein the upper and lower arches are closed and a second position wherein the upper and lower arches are open, said telescoping rod having a first end and a second end;
    a first attachment member rigidly coupled to said first end of said telescoping rod and having a first eyelet adapted to receive the first fastener to couple said first end to the lower molar; and
    a second attachment member rigidly coupled to said second end of said telescoping rod and having a second eyelet adapted to receive the second fastener to couple said second end to the upper molar, said first and second attachment members offset from said longitudinal axis in a first direction generally orthogonal to said longitudinal axis, a second direction substantially parallel to said longitudinal axis, and a third direction generally orthogonal to said first and second directions;
    wherein the first direction generally corresponds to a gingival-occlusal direction, the second direction generally corresponds to a mesial-distal direction, and the third direction generally corresponds to a labial-lingual direction when the orthodontic device is installed in the patient's mouth;
    wherein said first eyelet has a center offset from said longitudinal axis in the first direction by a first distance and said second eyelet has a center offset from said longitudinal axis in the first direction by a second distance, said second distance being greater than said first distance so that said telescoping rod is substantially parallel to an occlusal plane when in the first position.

21. The orthodontic device of claim 1 wherein said telescoping rod includes a first section coupled to said first attachment member and a second section coupled to said second attachment member, said first section being slidably received within said second section, said second section having an end surface, and said first attachment member having a disc-shaped portion configured to contact said end surface to limit movement of said first section into said second section.

* * * * *